United States Patent
Ince

(10) Patent No.: US 11,332,712 B2
(45) Date of Patent: May 17, 2022

(54) CELL CULTURE MEDIA AND METHOD FOR CULTURING BREAST CANCER CELLS

(71) Applicant: UNIVERSITY OF MIAMI, Miami, FL (US)

(72) Inventor: Tan Ince, Miami, FL (US)

(73) Assignee: UNIVERSITY OF MIAMI, Miami, FL (US)

( * ) Notice: Subject to any disclaimer, the term of this patent is extended or adjusted under 35 U.S.C. 154(b) by 96 days.

(21) Appl. No.: 16/598,991

(22) Filed: Oct. 10, 2019

(65) Prior Publication Data

US 2020/0040301 A1 Feb. 6, 2020

Related U.S. Application Data

(62) Division of application No. 15/687,150, filed on Aug. 25, 2017, now Pat. No. 10,465,166, which is a division of application No. 15/024,590, filed as application No. PCT/US2014/057188 on Sep. 24, 2014, now Pat. No. 9,777,256.

(60) Provisional application No. 61/881,695, filed on Sep. 24, 2013.

(51) Int. Cl.
  *C12N 5/071* (2010.01)
  *C12N 5/09* (2010.01)

(52) U.S. Cl.
  CPC ......... *C12N 5/0631* (2013.01); *C12N 5/0693* (2013.01); *C12N 2500/16* (2013.01); *C12N 2500/20* (2013.01); *C12N 2500/22* (2013.01); *C12N 2500/24* (2013.01); *C12N 2500/36* (2013.01); *C12N 2500/38* (2013.01); *C12N 2500/42* (2013.01); *C12N 2500/46* (2013.01); *C12N 2501/01* (2013.01); *C12N 2501/11* (2013.01); *C12N 2501/33* (2013.01); *C12N 2501/39* (2013.01); *C12N 2501/392* (2013.01)

(58) Field of Classification Search
  CPC ............................... C12N 2500/16
  See application file for complete search history.

(56) References Cited

U.S. PATENT DOCUMENTS

| | | |
|---|---|---|
| 8,252,591 B2 | 8/2012 | Ince et al. |
| 9,777,256 B2 | 10/2017 | Ince |
| 10,465,166 B2 | 11/2019 | Ince |

FOREIGN PATENT DOCUMENTS

| | | |
|---|---|---|
| EP | 2359857 A2 | 8/2011 |
| WO | WO-2012/129538 A1 | 9/2012 |

OTHER PUBLICATIONS

Briand et al., Effect of estrogen and antiestrogen on the human breast cancer cell line MCF-7 adapted to growth at low serum concentration, Can. Res., 44(3):1114-9 (1984).
Colston et al., Mechanisms implicated in the growth regulatory effects of vitamin D in breast cancer, Endocrine-Related Cancer, 9:45-59 (2001).
Darbre et al., Effect of estradiol on human breast cancer cells in culture, Hum. Breast. Can. Cell in Culture, 43(1):349-54 (1983).
Extended European Search Report issued in EP 14847994.2 dated Apr. 4, 2017.
Hickey et al., Minireview: The Androgen Receptor in Breast Tissues: Growth Inhibitor, Tumor Suppressor, Oncogene?, Molec. Endocrinol.,26(8):1252-67 (2012).
International Preliminary Report on Patentability, United States Patent Office, dated Mar. 29, 2016.
International Search Report and Written Opinion of the International Searching Authority, United States Patent Office, dated Dec. 4, 2014.
Labome, Fetal Bovine Serum: What is Fetal Bovine Serum?. Retrieved from the Internet, www.archIve.org:<http://www.archIve.org:> <URL: hdps://web.archive.org/web/20120804062606/http://www.labome.com/method/Fetal-Bovine-<http://web.archive.org/web/20120804062606/http://www.labome.com/method/Fetal-Bovine->Serum.html> (2012). [retrieved Aug. 4, 2012].
Lippman et al., The effects of androgens and antiandrogens on hormone-responsive human breast cancer in long-term tissue culture, Can. Res. 36(12):4610-8 (1976).
Ochi et al., Dextran-coated charcoal technique to make the hormone-free serum as a diluent for standard curve of radioimmunoassay, Endocrinol. Japan, 20(1),17 (1971).
Thakkar, et al., Vitamin D and androgen receptor-targeted therapy for triple-negative breast cancer, Breast Cancer Res Treat, Published Online Apr. 27, 2016.
Welsh, Targets of Vitamin D Receptor Signaling in the Mammary Gland, J. Bone Mineral Res., 22(2):V86-90 (2007).

*Primary Examiner* — Bin Shen
(74) *Attorney, Agent, or Firm* — Marshall, Gerstein & Borun LLP

(57) ABSTRACT

A cell culture medium comprising adenosine triphosphate; a carrier protein; cholesterol, linoleic acid, and lipoic acid; glutathione; at least one nucleotide salvage pathway precursor base; phosphoethanolamine; selenium; transferrin; triiodothyronine; all-trans-retinoic acid (ATRA) and vitamin C; zinc, magnesium, and copper; an agent that increases intracellular cAMP; epidermal growth factor (EGF); hydrocortisone; insulin; and charcoal stripped fetal bovine serum, wherein said cell culture medium is substantially free, if not entirely free, of vitamin D, androgenic hormones, androgenic ligands, estrogenic hormones, estrogenic ligands, and/or androgenic receptors.

8 Claims, 10 Drawing Sheets
(8 of 10 Drawing Sheet(s) Filed in Color)

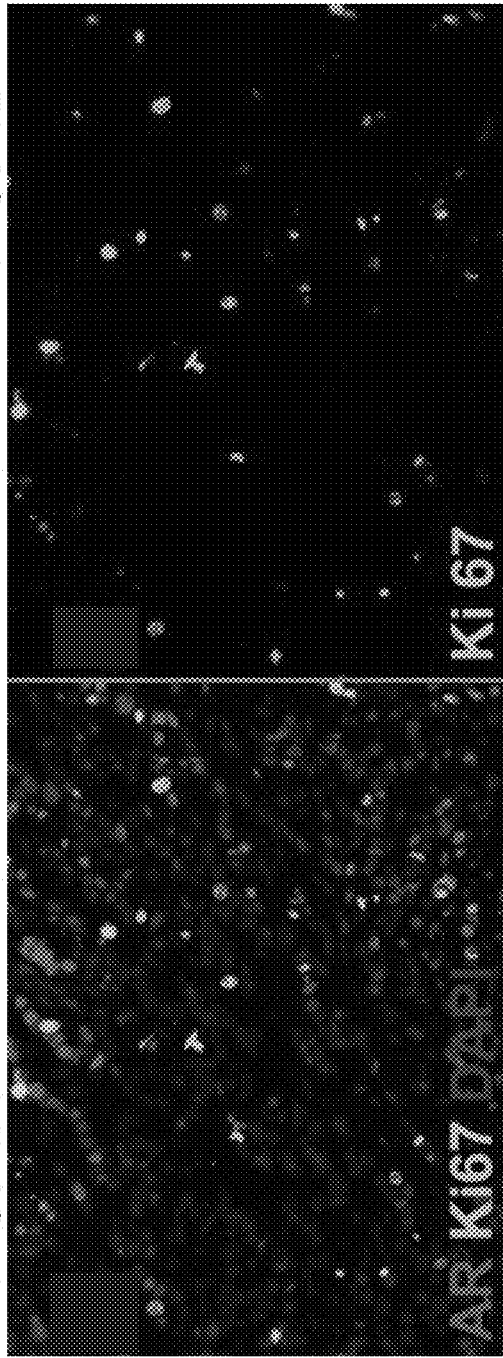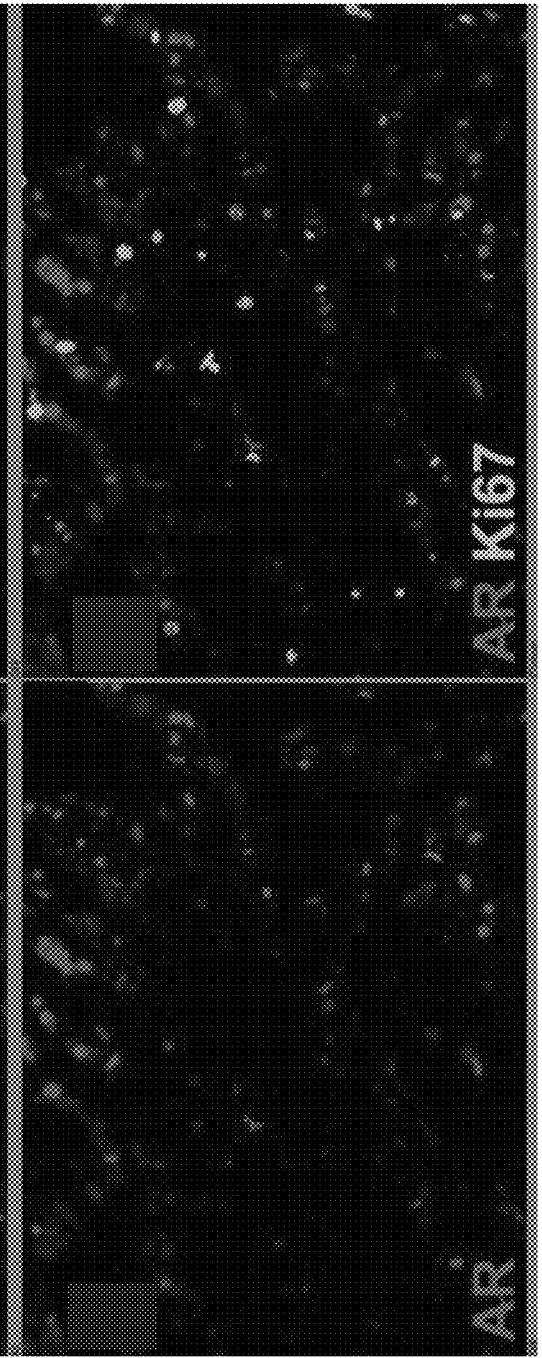

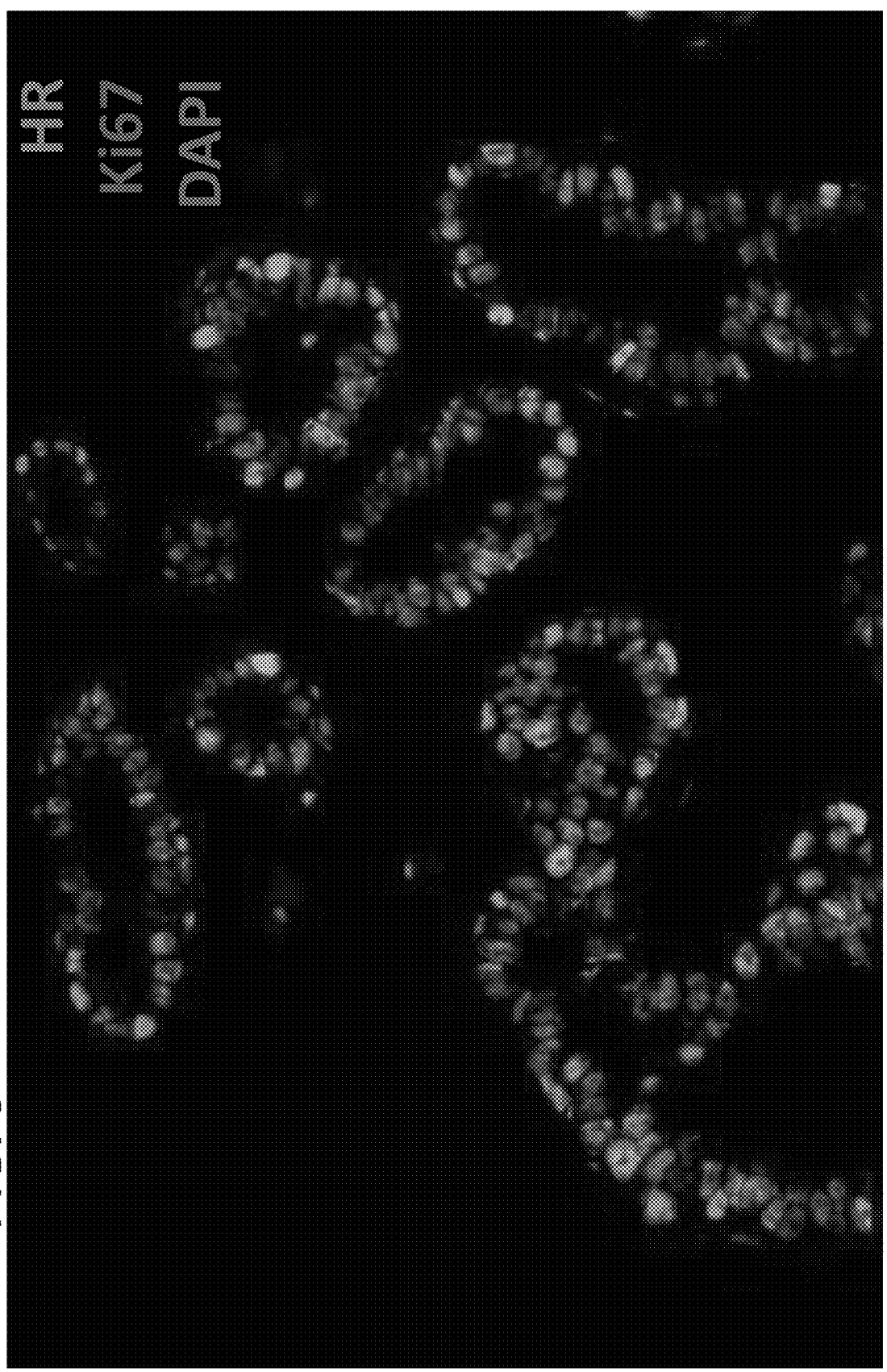

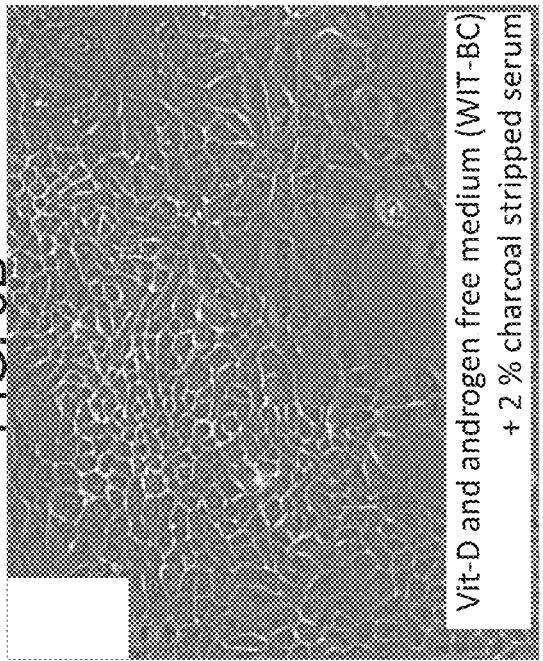
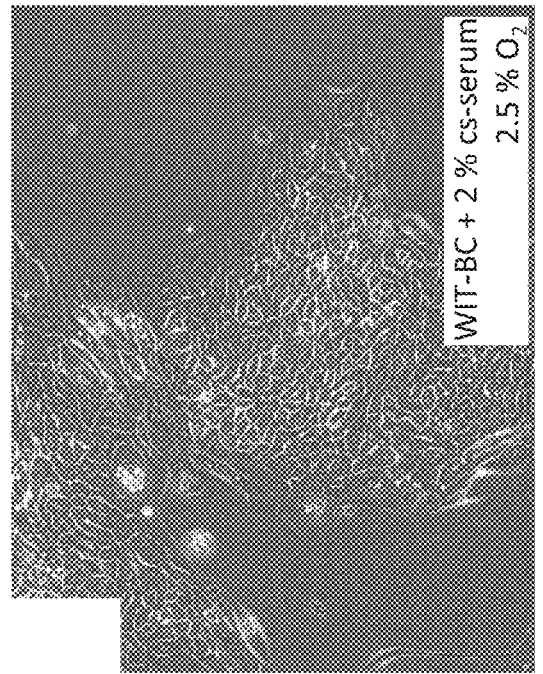
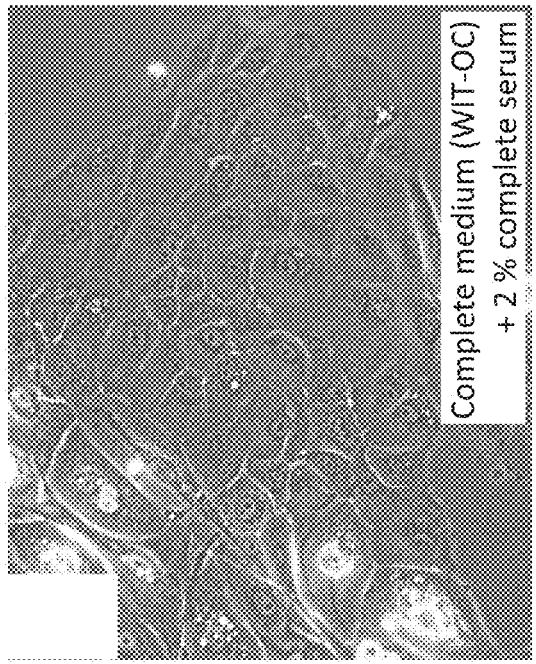
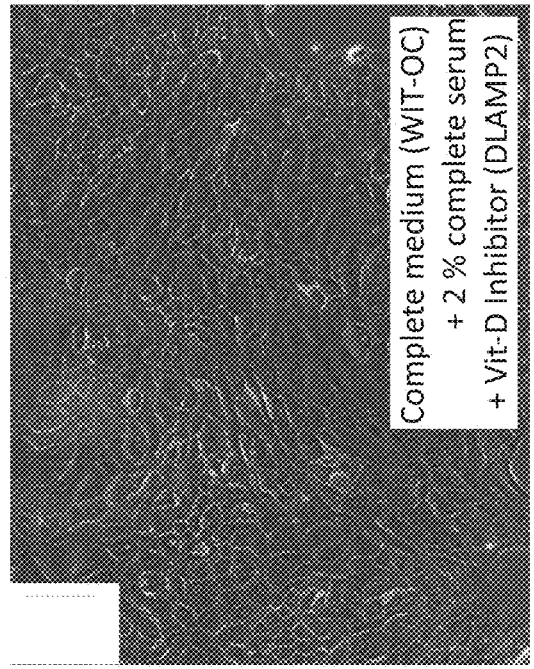

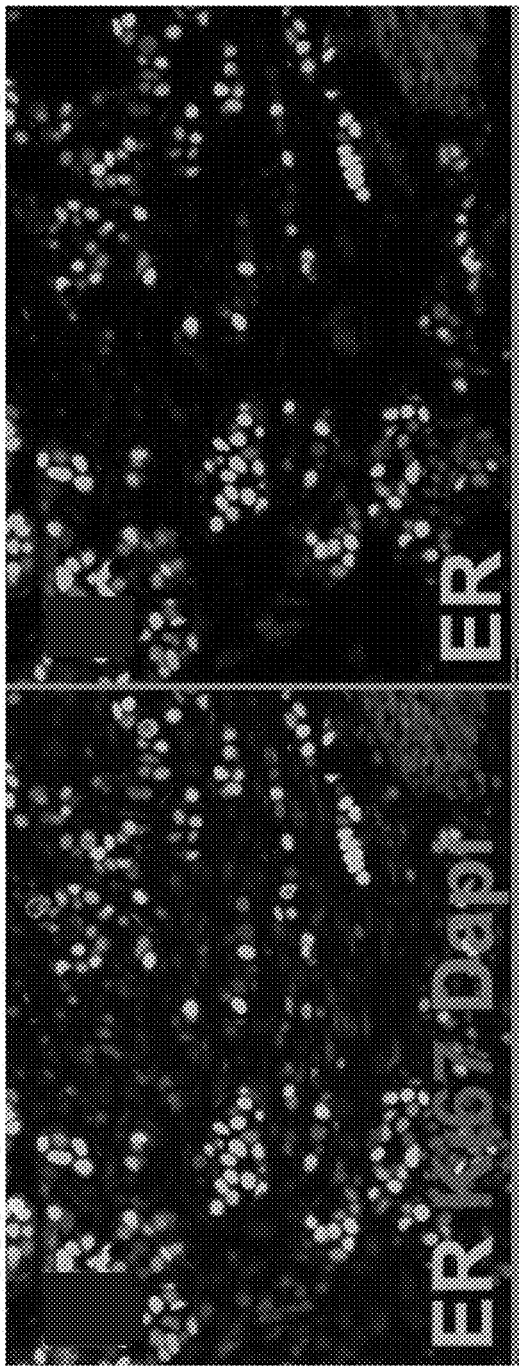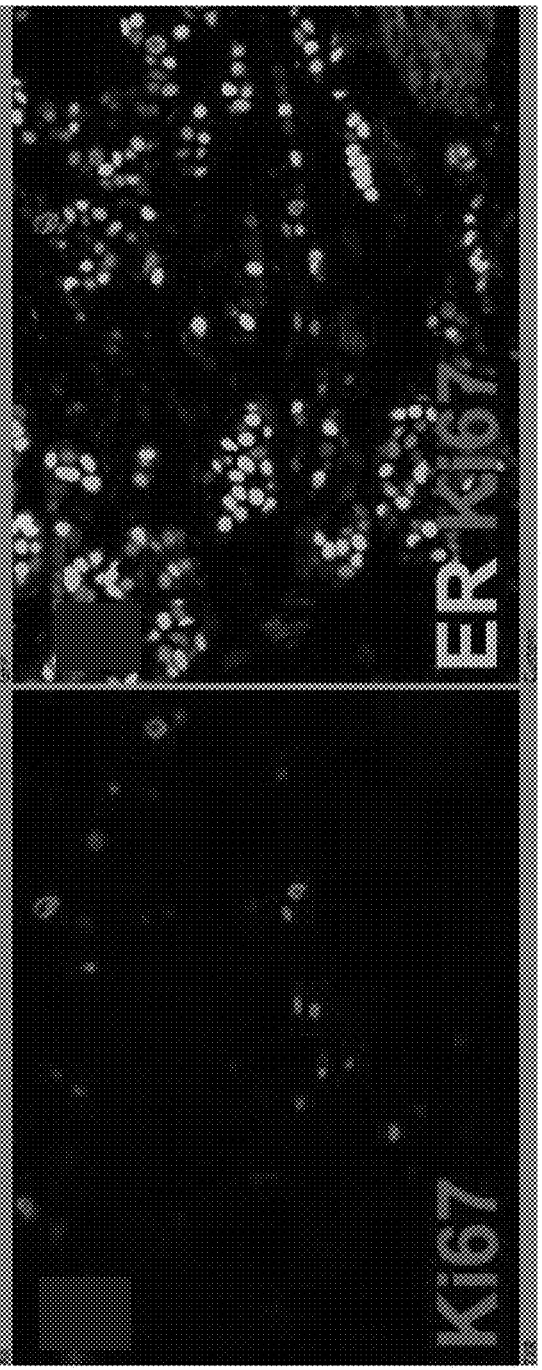
FIG. 10A  FIG. 10B  FIG. 10C  FIG. 10D

CELL CULTURE MEDIA AND METHOD FOR CULTURING BREAST CANCER CELLS

CROSS-REFERENCE TO RELATED APPLICATIONS

This Application is a Division of U.S. patent application Ser. No. 15/687,150, filed Aug. 25, 2017, which is a Division of U.S. patent application Ser. No. 15/024,590, filed Mar. 24, 2016 (35 USC § 371(c) date), which is a U.S. National Phase of International Patent Application No. PCT/US2014/057188, filed Sep. 24, 2014, which claims priority benefit under 35 USC § 119 of U.S. Provisional Patent Application No. 61/881,695, filed Sep. 24, 2013.

STATEMENT REGARDING FEDERALLY-SPONSORED RESEARCH AND DEVELOPMENT

This invention was made with government support under grant number CA146445 awarded by the National Institutes of Health. The government has certain rights in the invention.

BACKGROUND OF THE INVENTION

Field of the Invention

The present invention relates to medium for growing cells in culture under in vitro conditions, and more particularly, to growing breast cancer cell lines in culture such as for research and commercial purposes.

Description of the Related Art

Breast cancer is currently the second leading cause of death for women in the United States, and is the most commonly diagnosed cancer in women. Overall, 1 in 8 women in the U.S. will develop breast cancer in their lifetimes. Each year, over 40,000 women will die of breast cancer in the U.S. alone. Research in the area of breast cancer is therefore critical in better understanding the disease, to better enable diagnosis and treatments.

There are multiple forms or types of breast cancer, including ductal carcinoma in situ (DCIS) or intraductal carcinoma, invasive (or infiltrating) ductal carcinoma (IDC) and its various sub-types [including adenoid cystic (or adenocystic) carcinoma, low-grade adenosquamous carcinoma, medullary carcinoma, mucinous (or colloid) carcinoma, papillary carcinoma, tubular carcinoma, metaplastic carcinoma (including spindle cell and squamous), micropapillary carcinoma], mixed carcinoma (having features of both invasive ductal and lobular), invasive lobular carcinoma (ILC), inflammatory breast cancer (IBC), triple-negative breast cancers lacking estrogen and progesterone receptors and HER2 protein, Paget disease of the nipple, phyllodes tumors, angiosarcoma, as well as lobular carcinoma in situ, even though this is not considered cancer per se.

However, not all of these breast cancer cell types can be readily studied. For example, it is known that certain cell lines and/or cell types grow better in culture than others, and others do not grow in culture at all. Some cell lines, even cancerous cell lines, will not adhere to the cell culture plates to permit growth, and others do not take well to an ex vivo environment for reasons that are yet unknown, but may have to do with growing conditions such as temperature, humidity, percentage of oxygen or carbon dioxide in the atmosphere, nutrients, proximity or confluency of neighboring cells, intercellular signaling, scaffolding to attach, and others.

Previous work by this inventor, as described in U.S. Pat. No. 8,252,591, which is incorporated by reference herein in its entirety, identified cell culture medium useful for growing normal breast epithelial cells using the proprietary media claimed therein, and owned by Whitehead Institute for Biomedical Research (Cambridge, Mass.). However, breast cancer cells do not grow well in the media.

Similarly, the cell culture media disclosed and claimed in an International Application under the Patent Cooperation Treaty having International Application Number PCT/US2012/030446 and International Publication No. WO 2012/129538 A1, also resulting from previous work by this inventor and owned by Whitehead Institute for Biomedical Research (Cambridge, Mass.), and further, which is also incorporated by reference herein in its entirety, grew ovarian cancer cells well but was not suitable for breast cancer cells. Given that breast cancer is such a prevalent disease, and has many sub-types, a cell culture medium that can grow breast cancer cells in culture would be very beneficial to the assisting in the study of the disease and research into possible cures and treatments.

SUMMARY OF THE INVENTION

The present invention addresses and is intended to present a solution to the above-noted problems of culturing breast cancer cells ex vivo. The invention is directed to a cell culture medium, methods of use, and kits particularly suited for culturing breast cancer cells. The cell culture medium can be used to culture any type of breast cancer cell, from any sub-type of breast cancer, and therefore provides a powerful tool in advancing breast cancer research.

As demonstrated throughout the figures, this inventor discovered that the presence of vitamin D and androgenic hormones prevents proliferation of normal breast subtypes and breast cancer cells. Accordingly, the cell culture medium of the instant invention has been specially formulated to substantially eliminate, if not to fully eliminate vitamin D, androgenic hormones and ligands, estrogenic hormones and ligands, and/or androgen receptors. This is an extraordinary step, as virtually every commercially available cell culture media includes a variety of vitamins and hormones, including vitamin D, androgenic hormones, estrogenic hormones, androgenic ligands, estrogenic ligands, and/or androgen receptors.

All of the hormone families described here (estrogenic hormones, androgenic hormones, etc.) may have various natural and synthetic forms, or precursor and metabolite forms with similar activity, or molecules that inhibit these receptors. Thus, by androgenic we mean hormones or molecules that include, but are not limited to methyltestosterone, testosterone and derivatives thereof. Examples of andogren derivatives include but are not limited to esterified derivative of testosterone selected from the group consisting of testosterone cyclopentylpropionate (cipionate), testosterone enanthate (heptanoate), testosterone ethisterone (ethinyl), testosterone ketolaurate, testosterone phenylacetate, or testosterone propionate); as well as synthetic androgens such as methyltrienolone (e.g. mibolerone or methyltrienolone, R1881, [7 alpha, 17 alpha-dimethyl-19-nortestosterone]); or antiandrogens or precursors or metabolites of testosterone such as Dihydrotestosterone (DHT), or Androstenedione (4-androstenedione and 17-ketoestosterone), an intermediate for the production of androgen testosterone and the estrogens estrone and estradiol. The anti-androgenic drugs include but are not limited to hydroxyflutamide, cyproterone acetate, etc.

The estrogenic hormones include, but are not limited to, estrone (E1), estradiol (E2), and estriol (E3), or derivatives thereof. Examples of estrogen derivatives include but are not limited to an esterified derivative of β-estradiol selected from the group consisting of estradiol benzoate, estradiol cypionate, estradiol dipropionate, estradiol enanthate, estradiol ethynyl, estradiol undecylate, or estradiol valerate, as well as synthetic, non-steroidal or natural substances that have estrogenic activity including synthetic substances that are referred to xenoestrogens, plant chemicals with estrogenic activity called phytoestrogens and fungal chemicals known as mycoestrogens, or precursors or metabolites of estrogen hormones such as Dehydroepiandrosterone (DHEA, dehydroisoandrosterone or dehydroandrosterone). Estrogenic compounds span a spectrum from full agonists such as the natural endogenous hormone estrogen, mixed agonists/antagonistics such as tamoxifen, pure antagonists such as fulvestrant (ICI-182780), and aromatase inhibitors (AIs) which are a class of drugs that inhibit aromatase enzyme that synthesizes estrogen including but not limited to Anastrozole (Arimidex), Letrozole (Femara), etc.

Based on the original observations as disclosed in FIGS. 1 through 8, this inventor has very recently discovered that cell culture medium containing the typical complete serum is not effective in culturing normal breast cells or breast cancer cells because serum contains various hormones and vitamins including androgenic hormones and Vitamin D that inhibit breast cell proliferation. Therefore, the present cell culture medium uses charcoal stripped fetal bovine serum to remove the hormones while maintaining the other proteins, salts, sugars, and other factors needed for nutritive value.

Exemplary cell culture medium of the invention are defined by the following numbered paragraphs:

1. A cell culture medium comprising: (a) adenosine triphosphate; (b) a carrier protein; (c) cholesterol, linoleic acid, and lipoic acid; (d) glutathione; (e) at least one nucleotide salvage pathway precursor base; (f) phosphoethanolamine; (g) selenium; (h) transferrin; (i) triiodothyronine; (j) all-trans-retinoic acid (ATRA) and vitamin C; (k) zinc, magnesium, and copper; (l) an agent that increases intracellular cAMP; (m) epidermal growth factor (EGF); (n) hydrocortisone; (o) insulin; and (p) charcoal stripped fetal bovine serum; wherein said cell culture medium is substantially free of vitamin D.
2. The cell culture medium as recited in paragraph 1, wherein said medium is substantially free of any variety of vitamin D and vitamin D precursors, derivatives, or intermediates.
3. The cell culture medium as recited in paragraph 2, wherein said medium is substantially free of vitamin D2, vitamin D3, calciferol, calcitriol, drisdol, 7-dehydrocholesterol, cholecalciferol, 25-hydroxyvitamin D3, and 1, 25-dihydroxyvitamin D3.
4. The cell culture medium of paragraph 1 configured to support proliferation of breast cancer cells for at least about 15 population doublings.
5. A cell culture medium comprising: (a) adenosine triphosphate; (b) a carrier protein; (c) cholesterol, linoleic acid, and lipoic acid; (d) glutathione; (e) at least one nucleotide salvage pathway precursor base; (f) phosphoethanolamine; (g) selenium; (h) transferrin; (i) triiodothyronine; (j) all-trans-retinoic acid (ATRA) and vitamin C; (k) zinc, magnesium, and copper; (l) an agent that increases intracellular cAMP; (m) epidermal growth factor (EGF); (n) hydrocortisone; (o) insulin; and (p) charcoal stripped fetal bovine serum; wherein said cell culture medium is substantially free of androgenic hormones.
6. A cell culture medium comprising: (a) adenosine triphosphate; (b) a carrier protein; (c) cholesterol, linoleic acid, and lipoic acid; (d) glutathione; (e) at least one nucleotide salvage pathway precursor base; (f) phosphoethanolamine; (g) selenium; (h) transferrin; (i) triiodothyronine; (j) all-trans-retinoic acid (ATRA) and vitamin C; (k) zinc, magnesium, and copper; (l) an agent that increases intracellular cAMP; (m) epidermal growth factor (EGF); (n) hydrocortisone; (o) insulin; and (p) charcoal stripped fetal bovine serum; wherein said cell culture medium is substantially free of androgenic ligands.
7. A cell culture medium comprising: (a) adenosine triphosphate; (b) a carrier protein; (c) cholesterol, linoleic acid, and lipoic acid; (d) glutathione; (e) at least one nucleotide salvage pathway precursor base; (f) phosphoethanolamine; (g) selenium; (h) transferrin; (i) triiodothyronine; (j) all-trans-retinoic acid (ATRA) and vitamin C; (k) zinc, magnesium, and copper; (l) an agent that increases intracellular cAMP; (m) epidermal growth factor (EGF); (n) hydrocortisone; (o) insulin; and (p) charcoal stripped fetal bovine serum; wherein said cell culture medium is substantially free of vitamin D and androgenic hormones.
8. A cell culture medium comprising: (a) adenosine triphosphate; (b) a carrier protein; (c) cholesterol, linoleic acid, and lipoic acid; (d) glutathione; (e) at least one nucleotide salvage pathway precursor base; (f) phosphoethanolamine; (g) selenium; (h) transferrin; (i) triiodothyronine; (j) all-trans-retinoic acid (ATRA) and vitamin C; (k) zinc, magnesium, and copper; (l) an agent that increases intracellular cAMP; (m) epidermal growth factor (EGF); (n) hydrocortisone; (o) insulin; and (p) charcoal stripped fetal bovine serum; wherein said cell culture medium is substantially free of vitamin D and androgenic ligands.
9. A cell culture medium comprising: (a) adenosine triphosphate; (b) a carrier protein; (c) cholesterol, linoleic acid, and lipoic acid; (d) glutathione; (e) at least one nucleotide salvage pathway precursor base; (f) phosphoethanolamine; (g) selenium; (h) transferrin; (i) triiodothyronine; (j) all-trans-retinoic acid (ATRA) and vitamin C; (k) zinc, magnesium, and copper; (l) an agent that increases intracellular cAMP; (m) epidermal growth factor (EGF); (n) hydrocortisone; (o) insulin; and (p) charcoal stripped fetal bovine serum; wherein said cell culture medium is substantially free of androgenic hormones and androgenic ligands.
10. A cell culture medium comprising: (a) adenosine triphosphate; (b) a carrier protein; (c) cholesterol, linoleic acid, and lipoic acid; (d) glutathione; (e) at least one nucleotide salvage pathway precursor base; (f) phosphoethanolamine; (g) selenium; (h) transferrin; (i) triiodothyronine; (j) all-trans-retinoic acid (ATRA) and vitamin C; (k) zinc, magnesium, and copper; (l) an agent that increases intracellular cAMP; (m) epidermal growth factor (EGF); (n) hydrocortisone; (o) insulin; (p) at least one androgen receptor (AR) inhibitor; and (q) fetal bovine serum.
11. A cell culture medium comprising: (a) adenosine triphosphate; (b) a carrier protein; (c) cholesterol, linoleic acid, and lipoic acid; (d) glutathione; (e) at least one nucleotide salvage pathway precursor base; (f) phosphoethanolamine; (g) selenium; (h) transferrin; (i) triiodothyronine; (j) all-trans-retinoic acid (ATRA) and vitamin C; (k) zinc, magnesium, and copper; (l) an agent that increases intracellular cAMP; (m) epidermal growth factor (EGF); (n) hydrocortisone; (o) insulin; (p) at least one vitamin D receptor (VDR) inhibitor; and (q) fetal bovine serum.

12. A cell culture medium comprising: (a) adenosine triphosphate; (b) a carrier protein; (c) cholesterol, linoleic acid, and lipoic acid; (d) glutathione; (e) at least one nucleotide salvage pathway precursor base; (f) phosphoethanolamine; (g) selenium; (h) transferrin; (i) triiodothyronine; (j) all-trans-retinoic acid (ATRA) and vitamin C; (k) zinc, magnesium, and copper; (l) an agent that increases intracellular cAMP; (m) epidermal growth factor (EGF); (n) hydrocortisone; (o) insulin; (p) at least one androgen receptor (AR) inhibitor; (q) at least one vitamin D receptor (VDR) inhibitor; and (r) fetal bovine serum.

13. A cell culture medium comprising: (a) adenosine triphosphate; (b) a carrier protein; (c) cholesterol, linoleic acid, and lipoic acid; (d) glutathione; (e) at least one nucleotide salvage pathway precursor base; (f) phosphoethanolamine; (g) selenium; (h) transferrin; (i) triiodothyronine; (j) all-trans-retinoic acid (ATRA) and vitamin C; (k) zinc, magnesium, and copper; (l) an agent that increases intracellular cAMP; (m) epidermal growth factor (EGF); (n) hydrocortisone; (o) insulin; (p) at least one androgen receptor (AR) inhibitor; and (q) charcoal stripped fetal bovine serum; wherein said cell culture medium is substantially free of vitamin D, androgenic hormones, and androgenic ligands.

14. A cell culture medium comprising: (a) adenosine triphosphate; (b) a carrier protein; (c) cholesterol, linoleic acid, and lipoic acid; (d) glutathione; (e) at least one nucleotide salvage pathway precursor base; (f) phosphoethanolamine; (g) selenium; (h) transferrin; (i) triiodothyronine; (j) all-trans-retinoic acid (ATRA) and vitamin C; (k) zinc, magnesium, and copper; (l) an agent that increases intracellular cAMP; (m) epidermal growth factor (EGF); (n) hydrocortisone; (o) insulin; (p) at least one vitamin D receptor (VDR) inhibitor; and (q) charcoal stripped fetal bovine serum; wherein said cell culture medium is substantially free of vitamin D, androgenic hormones, and androgenic ligands.

15. A cell culture medium comprising: (a) adenosine triphosphate; (b) a carrier protein; (c) cholesterol, linoleic acid, and lipoic acid; (d) glutathione; (e) at least one nucleotide salvage pathway precursor base; (f) phosphoethanolamine; (g) selenium; (h) transferrin; (i) triiodothyronine; (j) all-trans-retinoic acid (ATRA) and vitamin C; (k) zinc, magnesium, and copper; (l) an agent that increases intracellular cAMP; (m) epidermal growth factor (EGF); (n) hydrocortisone; (o) insulin; (p) at least one androgen receptor (AR) inhibitor; (q) at least one vitamin D receptor (VDR) inhibitor; and (r) charcoal stripped fetal bovine serum; wherein said cell culture medium is substantially free of vitamin D, androgenic hormones, and androgenic ligands.

16. A cell culture medium comprising: (a) adenosine triphosphate; (b) a carrier protein; (c) cholesterol, linoleic acid, and lipoic acid; (d) glutathione; (e) at least one nucleotide salvage pathway precursor base; (f) phosphoethanolamine; (g) selenium; (h) transferrin; (i) triiodothyronine; (j) all-trans-retinoic acid (ATRA) and vitamin C; (k) zinc, magnesium, and copper; (l) an agent that increases intracellular cAMP; (m) epidermal growth factor (EGF); (n) hydrocortisone; (o) insulin; and (p) charcoal stripped fetal bovine serum; wherein said cell culture medium is substantially free of estrogenic hormones and estrogenic ligands.

17. A cell culture medium comprising: (a) adenosine triphosphate; (b) a carrier protein; (c) cholesterol, linoleic acid, and lipoic acid; (d) glutathione; (e) at least one nucleotide salvage pathway precursor base; (f) phosphoethanolamine; (g) selenium; (h) transferrin; (i) triiodothyronine; (j) all-trans-retinoic acid (ATRA) and vitamin C; (k) zinc, magnesium, and copper; (l) an agent that increases intracellular cAMP; (m) epidermal growth factor (EGF); (n) hydrocortisone; (o) insulin; and (p) charcoal stripped fetal bovine serum; wherein said cell culture medium is substantially free of vitamin D, estrogenic hormones, and estrogenic ligands.

18. A cell culture medium comprising: (a) adenosine triphosphate; (b) a carrier protein; (c) cholesterol, linoleic acid, and lipoic acid; (d) glutathione; (e) at least one nucleotide salvage pathway precursor base; (f) phosphoethanolamine; (g) selenium; (h) transferrin; (i) triiodothyronine; (j) all-trans-retinoic acid (ATRA) and vitamin C; (k) zinc, magnesium, and copper; (l) an agent that increases intracellular cAMP; (m) epidermal growth factor (EGF); (n) hydrocortisone; (o) insulin; and (p) charcoal stripped fetal bovine serum; wherein said cell culture medium is substantially free of androgenic hormones, androgenic ligands, estrogenic hormones, and estrogenic ligands.

19. A cell culture medium comprising: (a) adenosine triphosphate; (b) a carrier protein; (c) cholesterol, linoleic acid, and lipoic acid; (d) glutathione; (e) at least one nucleotide salvage pathway precursor base; (f) phosphoethanolamine; (g) selenium; (h) transferrin; (i) triiodothyronine; (j) all-trans-retinoic acid (ATRA) and vitamin C; (k) zinc, magnesium, and copper; (l) an agent that increases intracellular cAMP; (m) epidermal growth factor (EGF); (n) hydrocortisone; (o) insulin; and (p) charcoal stripped fetal bovine serum; wherein said cell culture medium is substantially free of vitamin D, androgenic hormones, androgenic ligands, estrogenic hormones, and estrogenic ligands.

The present invention is also directed to a method of using the cell culture medium as described herein, which involves isolating at least one breast cancer cell from cancerous tissue, contacting the at least one breast cancer cell with the breast cancer cell culture medium as described herein, and maintaining the at least one breast cancer cell in the breast cancer cell culture medium for a period of time and at conditions suitable for cell culture and growth.

An exemplary method of using cell culture medium of the invention is defined by the following numbered paragraph:

20. A method of culturing breast cancer cells comprising: obtaining a sample of breast cancer cells from cancerous breast tissue; adding an amount of the cell culture medium of numbered paragraph 1 above to the sample of breast cancer cells; and maintaining the sample of breast cancer cells in the cell culture medium of paragraph 1 at conditions appropriate for cell growth.

The present invention is also directed to a kit containing a predetermined amount of the breast cancer cell culture medium as described and claimed herein, and which may also include additional factors, additives, preservatives, antibacterial and/or anti-microbial agents, and other chemicals, compounds, and proteins as may be necessary or desired.

An exemplary kit of the invention is defined by the following numbered paragraph:

21. A kit for preparing the cell culture medium of numbered paragraph 1 above, the kit comprising: a first portion comprising components (a) through (k); and a second portion comprising components (l) through (p), wherein the first portion and the second portion comprise proportionate amounts of each of components (a) through (p) to produce the cell culture medium of paragraph 1.

These and other objects, features and advantages of the present invention will become clearer when the drawings as well as the detailed description are taken into consideration.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a fuller understanding of the nature of the present invention, reference should be had to the following detailed description taken in connection with the accompanying drawings in which:

In FIG. 1A, the cells that only express Ki67 are green and marks the proliferating cells. The cells that only express VDR are red. The overlap of these two fluorescent probes in the same cell would produce a yellow signal which is not detected, which indicates that notably VDR does not co-localize with Ki67. FIG. 1B illustrates an example of overlapping markers as a positive control in which some breast cells express both ER (green) and VDR (red), wherein the co-localized expression is are in yellow. Images were taken at approximately 200× magnification.

In FIG. 2A, the cells that only express Ki67 are red and marks the proliferating cells. The cells that only express AR are green. The overlap of these two fluorescent probes in the same cell would produce a yellow signal which is not detected, which indicates that notably AR does not co-localize with Ki67. FIG. 2B illustrates an example of overlapping markers as a positive control in which some breast cells express both AR (green) and VDR (red), wherein the co-localized expression is are in yellow. Images were taken at approximately 200× magnification.

FIG. 3A shows a merged image of staining with VDR (in red), proliferative marker Ki67 (in green) and counterstaining with DAPI (in blue) to mark nuclei. FIG. 3B shows Ki67 alone, FIG. 3C shows VDR alone, and FIG. 3D shows the VDR and Ki67 merge without nuclear stain. Images were taken at approximately 100× magnification. As is clear from FIGS. 3A and 3D, there is no co-localization of VDR and Ki67, indicating the proliferating cells do not express AR.

FIGS. 4A-4D shows immunofluorescence images of breast cancer tissue sections, demonstrating that the androgen receptor (AR) is not expressed in proliferating cells. FIG. 4A shows a merged image of staining with AR (in red), proliferative marker Ki67 (in green) and counterstaining with DAPI (in blue) to mark nuclei. FIG. 4B shows Ki67 alone, FIG. 4C shows AR alone, and FIG. 4D shows the AR and Ki67 merge without nuclear stain. Images were taken at approximately 100× magnification. As is clear from FIGS. 4A and 4D, there is no co-localization of AR and Ki67, indicating the proliferating cells do not express AR.

FIG. 5 shows an immunofluorescence image of a normal breast tissue section. An antibody to recognize any of ER, AR, and VDR was used (denoted herein as HR, shown in green), and was co-stained with Ki67 (in red) and DAPI (in blue). Images were taken at approximately 200× magnification. Once again, there is no co-expression of any of ER, AR, or VDR and Ki67, indicating these receptors are not present in proliferating breast cancer cells.

FIGS. 6A-6D show breast cancer cells under various conditions as imaged by DIC. FIG. 6A shows human breast cancer cells cultured in regular WIT-OCE medium that contains Vit-D and (0.1 mg/L) 2% fetal bovine serum that contains androgenic hormones in 5% $O_2$. In this medium there are significantly fewer cells that are large with abundant cytoplasm compared to FIGS. 6B-6D, consistent with growth arrested cells and inhibition of cell proliferation by FBS and vitamin D. FIG. 6B shows human breast cancer cells cultured in WIT-BC that is free of Vitamin D and 2% charcoal stripped fetal bovine serum that is free of androgenic hormones at 5% $O_2$. Compared to FIG. 6A there is a significant increase in cell numbers and the small cell size indicates minimal growth arrest. The growth conditions in FIGS. 6A and 6C were identical, except Vitamin D inhibitor (DLAMP2, 100 nM) was added to the culture medium in FIG. 6C, which partially reversed the growth inhibition observed in FIG. 6A. Routine cell culture is carried out at ambient air $O_2$ which is 18-21%. We discovered that breast cancer cells are best cultured in lower $O_2$ levels; less than 18% $O_2$, but greater that 2.5% $O_2$ (FIG. 6D). Compared to FIG. 6C there are fewer tumor cells in FIG. 6D, indicating that 5% $O_2$ levels are better than 2.5% $O_2$. The optimal level was approximately 5-10% $O_2$.

FIGS. 10A-10D shows immunofluorescence images of breast cancer tissue sections, demonstrating that the estrogen receptor (ER) is not expressed in proliferating cells. FIG. 10A shows a merged image of staining with ER (in green), proliferative marker Ki67 (in red) and counterstaining with DAPI (in blue) to mark nuclei. FIG. 10B shows ER alone, FIG. 10C shows Ki67 alone, and FIG. 10D shows the ER and Ki67 images merged without nuclear stain. Images were taken at approximately 100× magnification. As is clear from FIGS. 10A and 10D, there is no co-localization of ER and Ki67, indicating the proliferating cells do not express ER in this tumor. However, in some cases ER expressing cells and Ki67 cells overlapped in tumors (not shown); thus, depending of the tumor type we sometimes add estrogens in the medium and sometimes exclude it from the medium in ER+ tumors.

DETAILED DESCRIPTION OF THE PREFERRED EMBODIMENT

The present invention is directed to a cell culture medium for use in culturing any type of breast cancer cell. Specifically, the cell culture medium includes a number of proteins, vitamins, minerals, compounds, and molecules to provide nutritive value to cells and promote growth. Notably, and unique to the instant invention, the cell culture medium utilizes charcoal stripped fetal bovine serum and is free of vitamin D. In another embodiment of the present invention the cell culture medium may be substantially free of vitamin D. These are the aspects that optimize the cell culture medium for breast cancer cell culture.

More in particular, it has been discovered that the proliferating cells (Ki67+ cells) in human breast tumors were mutually exclusive with cells that expressed vitamin D receptor (VDR) and androgen receptor (AR) by immunostaining of normal human breast tissue and human breast tumor tissues. Based on this information it was deduced that vitamin D and androgenic hormones might be growth inhibitory for human breast cancers and may be counter-productive for the in vitro culture of these cells. Based on the foregoing, the formulation of the WIT medium previously develop for human ovarian carcinomas has been modified in order to optimize it for human breast carcinomas.

Figure 1B:
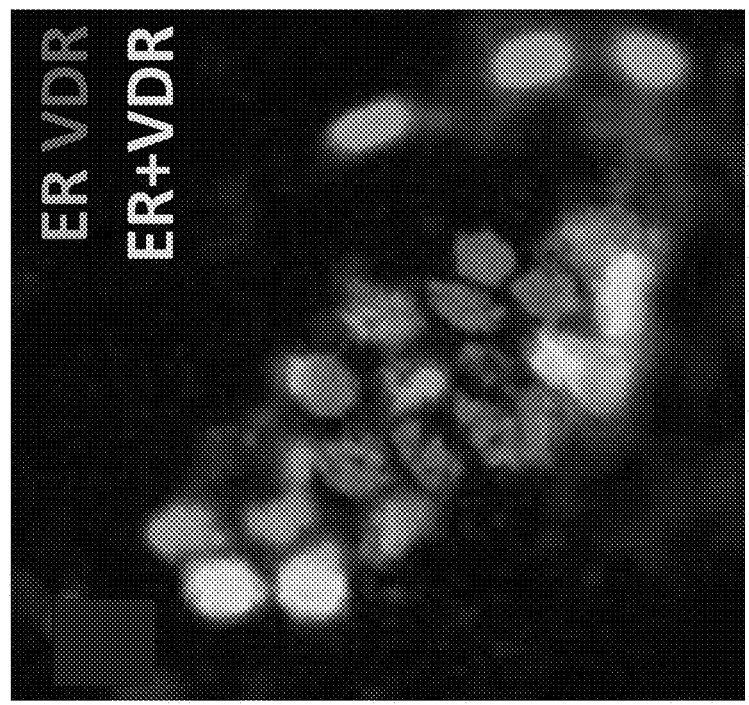
FIGS. 1A and 1B show immunofluorescence images of normal breast tissue sections, demonstrating that the vitamin D receptor (VDR) is not expressed in proliferating breast cancer cells. Normal human breast tissue sections were stained with primary antibodies for Ki67, a marker for proliferating cells, and VDR and/or estrogen receptor (ER).
Figure 1A:
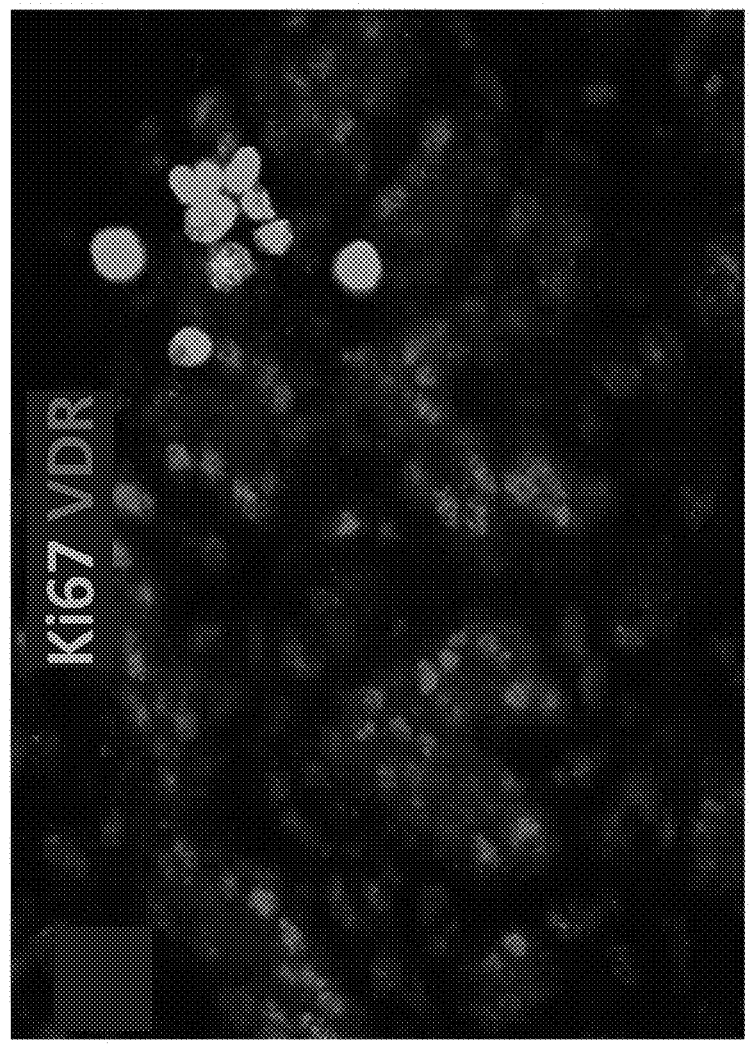
Figure 2B:
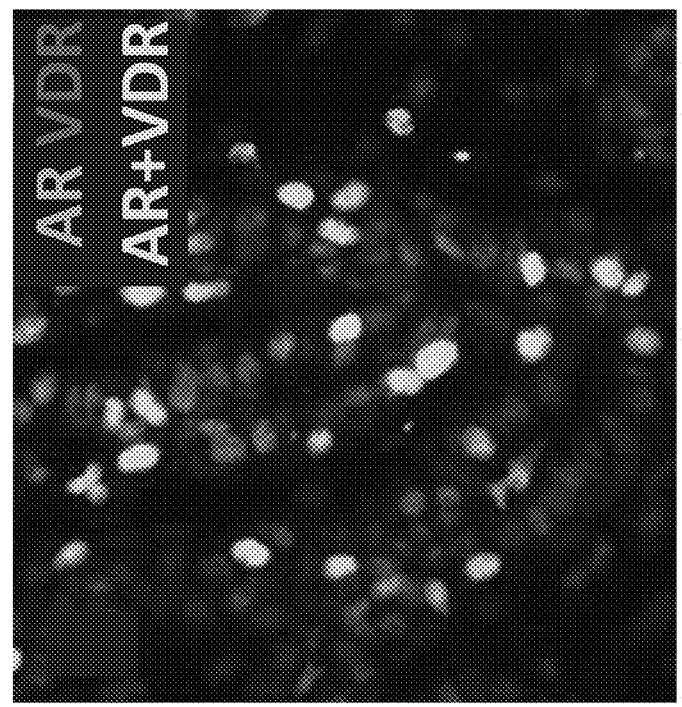
FIGS. 2A and 2B show immunofluorescence images of normal breast tissue sections, demonstrating that the androgen receptor (AR) is not expressed in proliferating breast cancer cells. Normal human breast tissue sections were stained with primary antibodies for Ki67, a marker for proliferating cells, and VDR and/or androgen receptor (AR).
Figure 2A:
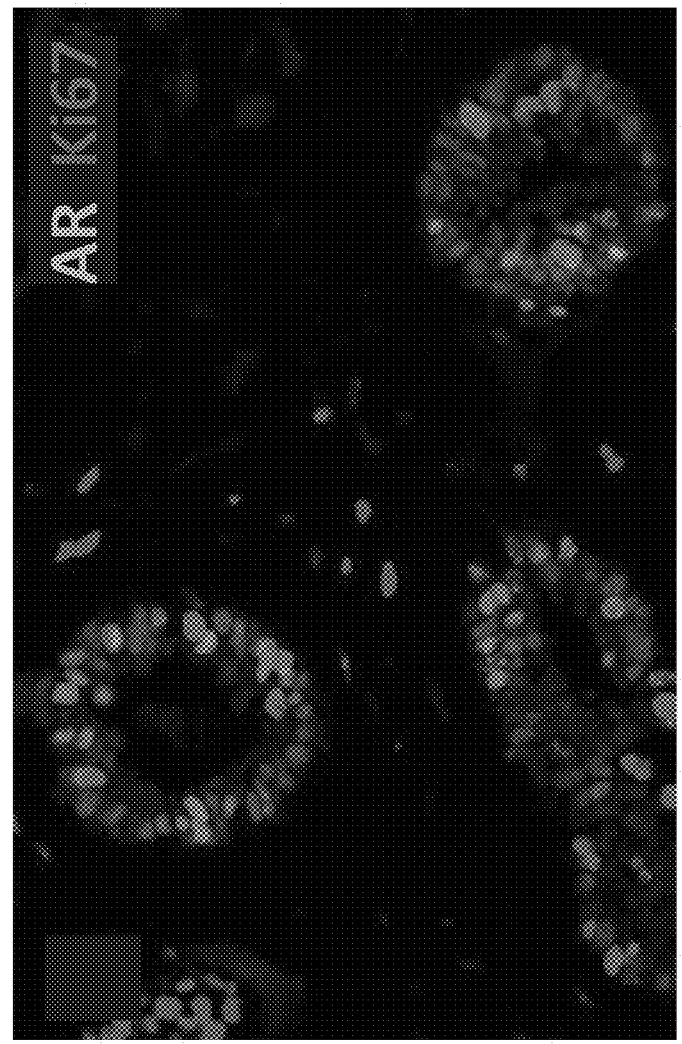
Figures 3A, 3B, 3C, 3D:
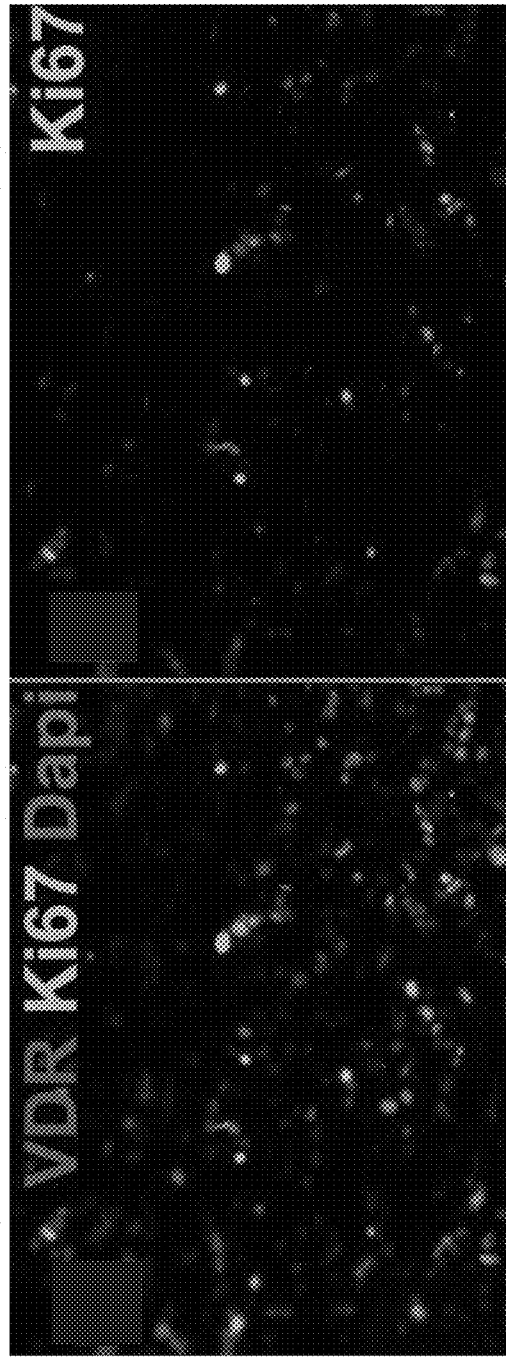
FIGS. 3A-3D show immunofluorescence images of breast cancer tissue sections, demonstrating that the Vitamin D receptor (VDR) is not expressed in proliferating cells.
Figure 7:
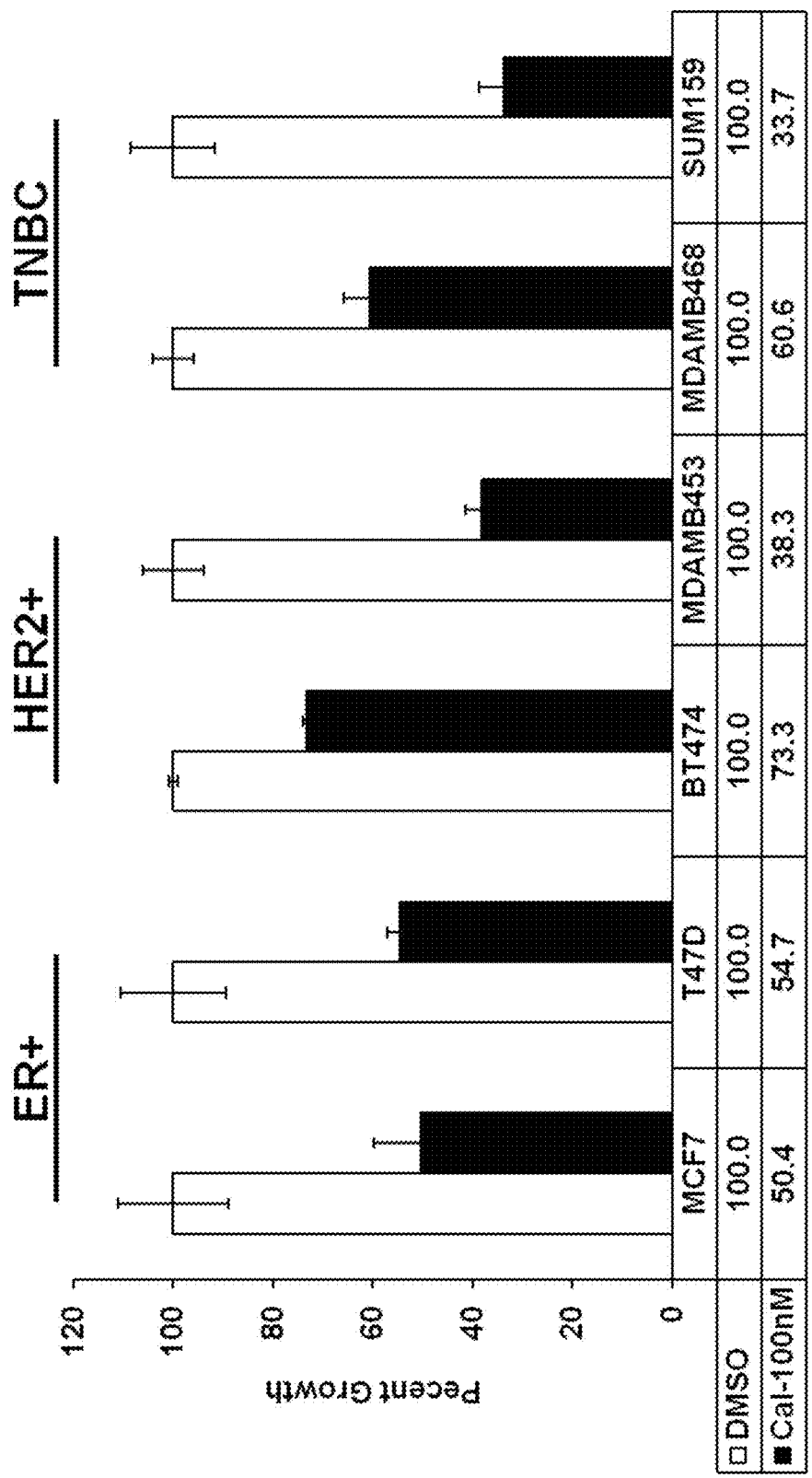
FIG. 7 shows the inhibitory effect of VDR agonist on breast cancer cell proliferation. In this experiment six different breast cancer cell lines that represent the three major breast cancer subtypes were tested, including ER+ Breast Cancer (MCF7, T47D), HER2+ Breast Cancer (BT474, MDA-MB-453), and Triple Negative Breast Cancer (TNBC) (MDA-MB-468, SUM159). These cell lines were cultured both with and without VDR agonist calcitriol. The breast cancer cell lines were allowed to attach overnight and Calcitriol (100 nM) was added to the media the next morning. Media was refreshed every two days and cells were stained with 0.1% trypan blue and counted using a Cellometer for proliferation assays after 4 days.
Figure 8:
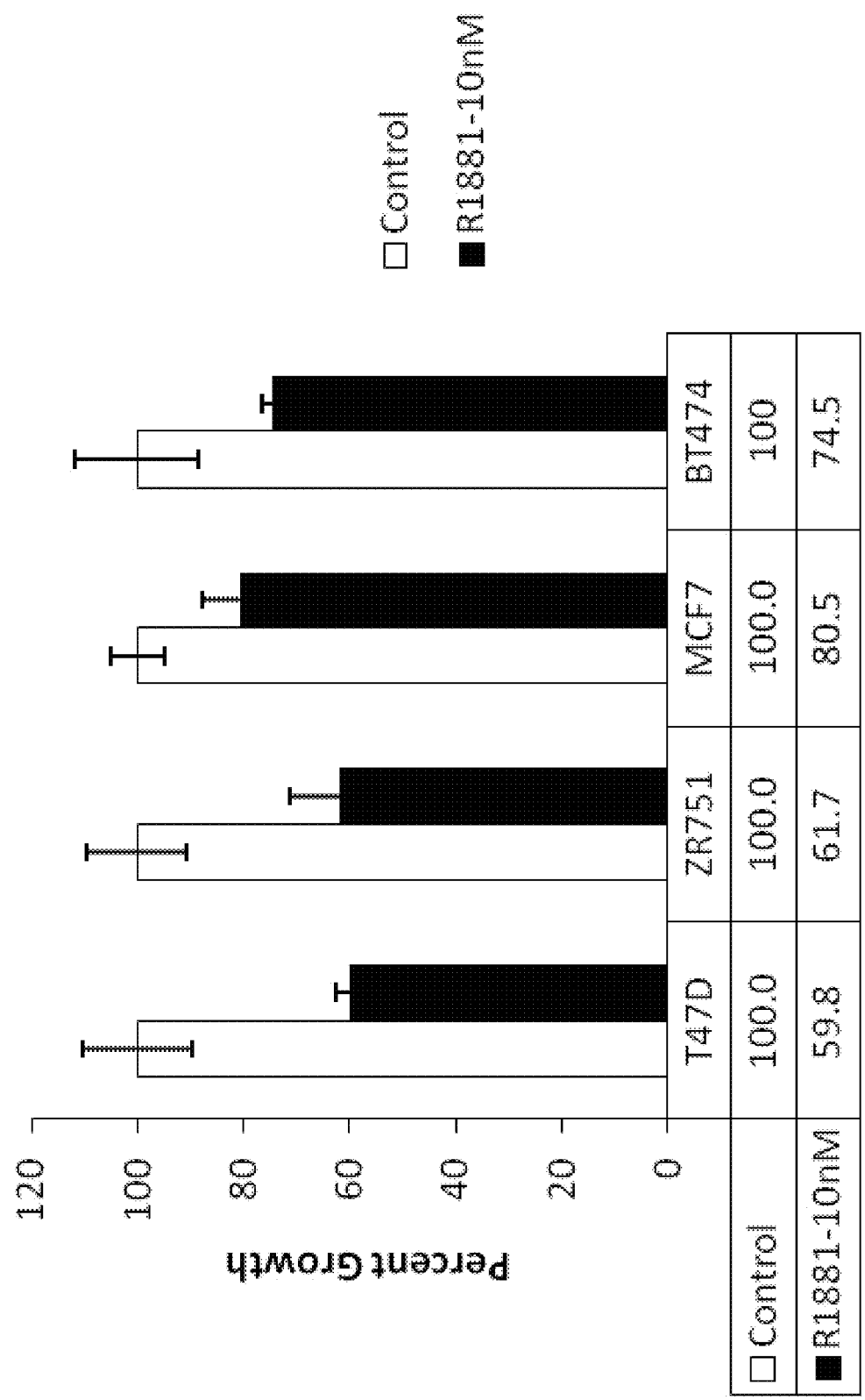
FIG. 8 shows the inhibitory effect of AR agonist on breast cancer cell proliferation. Four different breast cancer cell lines (T47D, ZR751, MCF7 and BT474) were cultured both with and without AR agonist R18811. The breast cancer cell lines were allowed to attach overnight in phenol-red free DMEM with 5% charcoal stripped fetal bovine serum. After 3 days, an AR agonist R1881 (10 nM) and 17 beta-Estradiol (10 nM) were added to the media. Cells were maintained in this medium for 4 days after which they were trypsinized, stained with 0.1% trypan blue and counted using a Cellometer. All the conditions were carried out in triplicate and the experiments were repeated at least twice.
Figure 9:
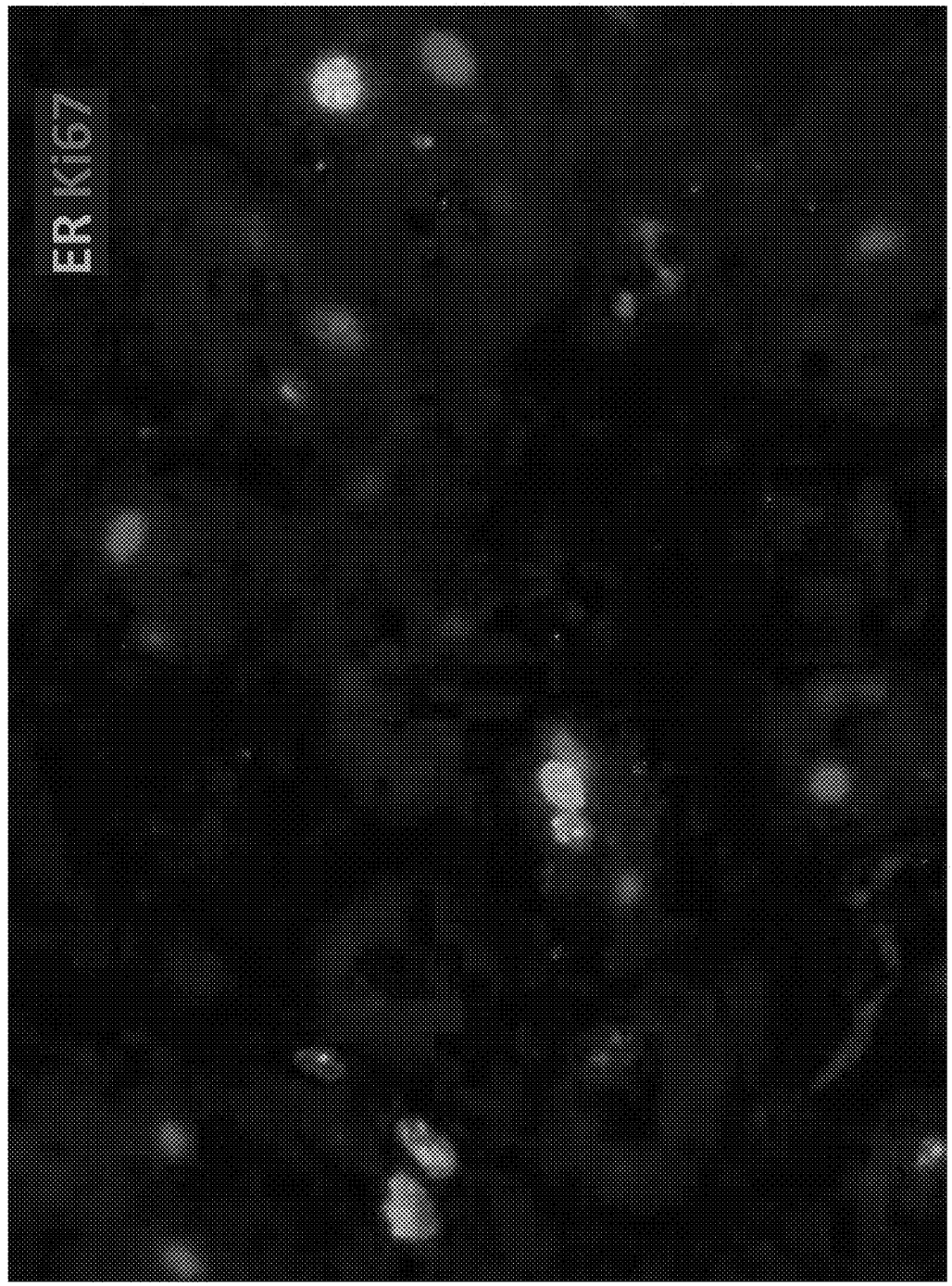
FIG. 9 shows immunofluorescence images of normal breast tissue sections, demonstrating that the estrogen receptor (ER) is not expressed in proliferating cells. The merged image shows staining with ER (in green) and the proliferative marker Ki67 (in red). Images were taken at approximately 100× magnification. As is clear there is no co-localization of ER and Ki67 which would produce a yellow signal, indicating the proliferating cells do not express ER.

In brief, FIGS. 1A through 5 and FIGS. 9 through 10D illustrate the expression patterns of vitamin D receptor (VDR), androgen receptor (AR), and estrogen receptor (ER) in normal and malignant human breast tissue. FIGS. 6A through 8 illustrate the effect of the ligands for these receptors on normal and malignant breast cell proliferation in culture.

These figures show that the proliferating Ki67 cells are mutually exclusive with vitamin D receptor (VDR) positive cells, both in normal breast (FIGS. 1A-1B) and breast cancer tissue (FIGS. 3A-3D). The Ki67 cells are also mutually exclusive with androgen receptor (AR) positive cells, both in normal breast (FIGS. 2A-2B) and breast cancer tissue (FIGS. 4A-4D). In addition, cells that are double AR/VDR positive were also mutually exclusive with proliferating cells (FIG. 5). The Ki67 cells are also mutually exclusive with estrogen receptor (ER) positive cells, both in normal breast tissue (FIG. 9) and breast cancer tissue (FIGS. 10A-10B).

In at least some embodiments, the cell culture medium is substantially free of one or more components, and in at least one embodiment, "substantially free" refers to a low amount of the component that has no statistically significant effect on cell growth. In at least some embodiments, "substantially free" means less than 1%, 0.1%, 0.01%, 0.001%, or 0.0001% v/v of a liquid or w/v of a solute. In at least some other embodiments, "substantially free" means a concentration of less than 0.01, 0.001, 0.0001, 0.00001, 0.000001, or 0.0000001 mg/L, and in yet other embodiments, "substantially free" means a concentration of less than 10 nM, 1 nM, 100 pM, or 1 pM.

To begin, the present cell culture medium may contain many ingredients already found in commercially available cell culture media. For example, in at least one embodiment the cell culture medium includes adenosine triphosphate (ATP) as an energy source for the cells.

In at least one embodiment, the cell culture medium includes at least one carrier protein, certain hormones such as hydrocortisone and/or one or more growth factors such as insulin and EGF (epidermal growth factor).

In at least one further embodiment, the cell culture medium includes one or more lipid synthesis precursors, such as cholesterol, linoleic acid, lipoic acid, and/or O-phosphoryl ethanolamine.

In another embodiment, the cell culture medium also includes one or more antioxidant, such as, but not limited to, glutathione, glutathione (reduced), and/or vitamin C (ascorbic acid). In one further embodiment, the cell culture medium comprises one or more trace metals to supplement the antioxidant(s), such as, but not limited to zinc, selenium, chromium, copper, manganese and/or magnesium.

At least one embodiment of the cell culture medium comprises at least one nucleotide salvage pathway precursor base including but not limited to hypoxanthine, xanthine, adenine, guanine and/or thymidine.

Yet one further embodiment of the cell culture medium of the present invention comprises an amount of phosphoethanolamine.

One other embodiment of the cell culture medium of the present invention comprises transferrin.

At least one further embodiment of the cell culture medium includes triiodothyronine, and another embodiment comprises an amount of vitamin A.

Another embodiment of the present cell culture medium comprises at least one agent that increases intracellular cAMP, and in one further embodiment, the agent that increases intercellular cAMP comprises cholera toxin.

One embodiment of the cell culture medium of the present invention further comprises at least one epidermal growth factor (EGF).

A further embodiment of the present cell culture medium includes an amount of hydrocortisone, and yet another embodiment comprises insulin.

At least one embodiment of the cell culture medium in accordance with the present invention comprises fetal bovine serum (FBS), and in one preferred embodiment, the cell culture medium of the present invention comprises fetal bovine serum that has been filtered through activated charcoal, referenced herein as charcoal stripped fetal bovine serum (csFBS).

The cell culture medium in accordance with the present comprises components which are substantially free of vitamin D, and in at least one embodiment, the cell culture medium of the present invention is itself substantially free of vitamin D.

In at least one further embodiment, the cell culture medium of the present invention is substantially free of vitamin A, as Retinol, and in yet one further embodiment, the cell culture medium in accordance with the present invention comprises an amount of all-trans-retinoic acid (ATRA).

The methods and compositions herein described and the related kits are further illustrated in the following examples, which are provided by way of illustration and are not intended to be limiting. It will be appreciated that variations in proportions and alternatives in elements of the components shown will be apparent to those skilled in the art and are within the scope of embodiments of the present invention. Theoretical aspects are presented with the understanding that Applicants do not seek to be bound by the theory presented. All parts or amounts, unless otherwise specified, are by weight.

EXAMPLES

Example 1

The base WIT cell culture medium contains 0.1 mg/L Calciferol (vitamin D2) and this medium is supplemented with 2-5% fetal bovine serum (FBS) to culture human ovarian carcinoma cells (WIT-OC medium). It was hypothesized that both of these components should be removed from the cell culture medium for the successful culture of human breast cancer cells because FBS contains vitamins and hormones such as vitamin D and androgens. Hence, FBS would inhibit the proliferation of breast tumor cells. Thus, charcoal stripped fetal bovine serum (csFBS) was utilized to culture breast tumor cells because activated carbon removes non-polar material such as lipophilic (lipid-related) materials (virus, certain growth factors, hormones and cytokines) regardless of molecular weight but has little effect on salts, glucose, amino acids, etc. The WIT-OC medium also contained vitamin A acetate (Retinol) which is a weaker form of vitamin A, compared to all-trans-retinoic acid (ATRA). In preliminary experiments, it was determined that this stronger form of vitamin A (ATRA) was promoting the growth of the breast tumor cells.

Thus, in order to formulate a cell culture medium optimized to culture human breast tumor cells, as opposed to ovarian tumors, and other tumors, a WIT cell culture medium was prepared without any vitamin D, vitamin A, or androgens, and this medium was supplemented 100 nM ATRA, and 0.5-2% charcoal stripped fetal bovine serum (csFBS). We refer to this medium as WIT-BC, or WIT-BCe when estrogen is added.

Interestingly, while complete serum does not inhibit proliferation of ovarian tumor cells, it did significantly reduce the proliferation of breast tumor cells. In addition, while a weak form of vitamin A (Retinol) was adequate to culture ovarian tumors, a stronger form of vitamin A (ATRA) was needed for the optimum culture if human breast tumor cells. Tables Table 1 presents the results obtained from tests conducted in accordance with Example 1.

TABLE 1

| | WIT (base medium) | Ovarian Tumors | | Breast Tumors | |
|---|---|---|---|---|---|
| | | ER− WIT-OC | ER+ WIT-OCe | ER− WIT-BC | ER+ WIT-BCe |
| Vitamin D | + | + | + | − | − |
| Vitamin A (Retinol) | + | + | + | − | − |
| All-trans Retinoic Acid | − | − | − | + | + |
| Fetal Bovine Serum | − | + | + | − | − |
| Charcoal Striped Fetal Bovine Serum | − | − | − | + | + |
| Estrogen | − | − | + | − | +/− |

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

REFERENCES

Ochi, Y., Shiomi, K., Hachiya, T., Yoshimura, M., and Miyakai, T., Dextran-coated charcoal technique to make the hormone-free serum as a diluent for standard curve of radioimmunoassay. *Endocrinol. Japan*, 1971, 20(1), 1~7.

INCORPORATION BY REFERENCE

All publications, patents, and patent publications referenced herein are hereby incorporated by reference in their entirety as if each individual publication, patent, and patent publication was specifically and individually indicated to be incorporated by reference.

What is claimed is:

1. A cell culture medium comprising:
    (a) adenosine triphosphate; (b) a carrier protein; (c) cholesterol, linoleic acid, and lipoic acid; (d) glutathione; (e) at least one nucleotide salvage pathway precursor base; (f) phosphoethanolamine; (g) selenium; (h) transferrin; (i) triiodothyronine; (j) all-trans-retinoic acid (ATRA) and vitamin C; (k) zinc, magnesium, and copper; (l) an agent that increases intracellular cAMP; (m) epidermal growth factor (EGF); (n) hydrocortisone; (o) insulin; and (p) charcoal-stripped fetal bovine serum; and
    wherein said cell culture medium is substantially free of estrogenic hormones and estrogenic ligands.

2. The cell culture medium of claim 1, wherein said culture medium is substantially free of vitamin D.

3. The cell culture medium of claim 2, wherein said culture medium is substantially free of androgenic hormones and androgenic ligands.

4. A method of culturing breast cancer cells comprising,
    obtaining a sample of breast cancer cells from cancerous breast tissue,
    adding an amount of the cell culture medium of claim 3 to the sample of breast cancer cells, and
    maintaining the sample of breast cancer cells in the cell culture medium of claim 3 at conditions appropriate for cell growth.

5. A method of culturing breast cancer cells comprising,
obtaining a sample of breast cancer cells from cancerous breast tissue,
adding an amount of the cell culture medium of claim 2 to the sample of breast cancer cells, and
maintaining the sample of breast cancer cells in the cell culture medium of claim 2 at conditions appropriate for cell growth.

6. The cell culture medium of claim 1, wherein said culture medium is substantially free of androgenic hormones and androgenic ligands.

7. A method of culturing breast cancer cells comprising,
obtaining a sample of breast cancer cells from cancerous breast tissue,
adding an amount of the cell culture medium of claim 6 to the sample of breast cancer cells, and
maintaining the sample of breast cancer cells in the cell culture medium of claim 6 at conditions appropriate for cell growth.

8. A method of culturing breast cancer cells comprising,
obtaining a sample of breast cancer cells from cancerous breast tissue,
adding an amount of the cell culture medium of claim 1 to the sample of breast cancer cells, and
maintaining the sample of breast cancer cells in the cell culture medium of claim 1 at conditions appropriate for cell growth.

\* \* \* \* \*